United States Patent
Blocher et al.

(10) Patent No.: US 9,974,623 B2
(45) Date of Patent: May 22, 2018

(54) METHOD AND APPARATUS FOR MOUNTING A SHEATH ONTO THE DISTAL END OF A SURGICAL SHAFT INSTRUMENT

(75) Inventors: Martin Blocher, Stockach-Espasingen (DE); Robin Merz, Furtwangen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 1626 days.

(21) Appl. No.: 13/193,161

(22) Filed: Jul. 28, 2011

(65) Prior Publication Data

US 2012/0079701 A1 Apr. 5, 2012

(30) Foreign Application Priority Data

Jul. 28, 2010 (DE) .................. 10 2010 032 606

(51) Int. Cl.
*B23P 15/00* (2006.01)
*A61B 46/17* (2016.01)
*A61B 46/10* (2016.01)
*A61B 17/02* (2006.01)
*A61B 17/24* (2006.01)
*A61B 90/00* (2016.01)

(52) U.S. Cl.
CPC .............. *A61B 46/17* (2016.02); *A61B 46/10* (2016.02); *A61B 17/0218* (2013.01); *A61B 17/24* (2013.01); *A61B 2090/0813* (2016.02); *A61B 2090/08021* (2016.02); *Y10T 29/4987* (2015.01); *Y10T 29/53657* (2015.01)

(58) Field of Classification Search
CPC ...................................................... B23P 15/00
USPC .................. 29/255, 270, 278, 238, 239, 235
See application file for complete search history.

(56) References Cited

U.S. PATENT DOCUMENTS

| 2,503,426 | A | * | 4/1950 | Tower | 29/283 |
| 4,057,886 | A | * | 11/1977 | Brass | 29/235 |
| 4,877,228 | A | * | 10/1989 | Ripert | 269/156 |
| 5,564,431 | A | | 10/1996 | Seward | |
| 5,875,534 | A | * | 3/1999 | Jackson | 29/255 |
| 6,049,960 | A | | 4/2000 | Pilling et al. | |

(Continued)

FOREIGN PATENT DOCUMENTS

DE 202007014102 U1 2/2008

OTHER PUBLICATIONS

German Search Report; Application No. 10 2010 032 606.2; dated Mar. 22, 2011; 4 pages.

(Continued)

*Primary Examiner* — Lee D Wilson
(74) *Attorney, Agent, or Firm* — Whitmyer IP Group LLC (57) ABSTRACT

A method for mounting a sheath onto the distal end of a surgical shaft instrument, in particular the tool tip of a dilation instrument. The method makes handling easy and allows the sheath to be fastened on the instrument in a rapid manner sparing of material, characterized by these steps: a) fastening the sheath on an apparatus for mounting a sheath onto the distal end of a surgical shaft instrument; b) radially widening at least the proximal end of the sheath and inserting the distal end of the surgical shaft instrument into the widened sheath c) transferring the sheath from the apparatus to the distal end of the surgical shaft instrument; and d) removing the distal end of the surgical shaft instrument from the apparatus. The invention also relates to an apparatus to perform this method.

15 Claims, 7 Drawing Sheets

(56) References Cited

U.S. PATENT DOCUMENTS

| | | |
|---|---|---|
| 6,357,735 B2 * | 3/2002 | Haverinen .................... 269/43 |
| 7,496,999 B2 * | 3/2009 | Robarge ........................ 29/265 |
| 2007/0149850 A1 | 6/2007 | Spivey et al. |
| 2009/0234374 A1 | 9/2009 | Gabel et al. |
| 2009/0234380 A1 | 9/2009 | Gabel et al. |

OTHER PUBLICATIONS

European Search Report Application No. 11175029.5 Completed Date: Nov. 3, 2015; dated Nov. 9, 2015 7 pages.

* cited by examiner

METHOD AND APPARATUS FOR MOUNTING A SHEATH ONTO THE DISTAL END OF A SURGICAL SHAFT INSTRUMENT

CROSS-REFERENCE TO RELATED APPLICATIONS

The present application claims priority of German patent application No. 10 2010 032 606.2 filed on Jul. 28, 2010.

FIELD OF THE INVENTION

The invention relates to a method for mounting a sheath on a distal end of a surgical shaft instrument, in particular the tool tip of a dilation instrument. In addition the invention relates to an apparatus for performing this method.

BACKGROUND OF THE INVENTION

Dilation instruments are used, for example, in endoscopic ENT surgery in order to widen a patient's frontal sinus and to remove osseous growths in the frontal cavity.

To prevent the penetration of tissue into the dilation mechanism and to allow the resetting of segments of the dilation mechanism, a sheath can be pulled over the distal end of the shaft instrument that is equipped with the dilation tool. Because of the small structural size of the endoscopic instrument, it is very difficult to pull the sheath manually over the distal instrument tip while simultaneously guarding against damage to the sheath from this pulling motion, because the tools often comprise sharp-edged sections on the instrument tip.

Consequently it is the object of the invention to provide a method for mounting a sheath onto the distal end of a surgical shaft instrument, said method being simple to operate and making possible a fastening of the sheath on the instrument tip that is both rapid and protects the material. In addition it is an object of the invention to provide an apparatus for performing the method.

SUMMARY OF THE INVENTION

The object of the invention is achieved according to the invention by means of these steps in the method:
  a) fasten the sheath on an apparatus for mounting a sheath onto the distal end of a surgical shaft instrument,
  b) radially widen at least the proximal end of the sheath and insert the distal end of the surgical shaft instrument into the widened sheath,
  c) transfer the sheath from the apparatus for mounting a sheath onto the distal end of a surgical shaft instrument to the distal end of the surgical shaft instrument, and
  d) remove the distal end of the surgical shaft instrument provided with the sheath from the apparatus for mounting a sheath onto the distal end of a surgical shaft instrument.

The inventive method allows the sheath to be pulled in simple manner onto the instrument tip while simultaneously sparing the material of the sheath. The radial widening of the sheath in step b) of the method allows simple insertion of the instrument tip into the sheath without the danger of damaging the sheath material with the instrument tip.

According to a preferred embodiment of the invention, it is proposed that the radial widening of the proximal end of the sheath in step b) of the method should be performed directly or indirectly by the distal end of the surgical shaft instrument.

Fulfillment of the object concerning the apparatus is characterized according to the invention by a base body comprising at least two spreading elements, such that the sheath can be fastened on the spreading elements and an insertion opening for receiving the distal end of the surgical shaft instrument is configured between the spreading elements. By fastening the sheath on the spreading elements of the pulling apparatus, no additional manual actuation is required to transmit the sheath to the instrument tip.

With a first embodiment of the invention, it is proposed that the spreading elements should be mounted on a base body.

According to a preferred embodiment of the invention, it is proposed that the at least two spreading elements should be mounted on the base body to be radially displaceable to the insertion opening so that the proximal-side end of the sheath that can be fastened on the spreading elements should be radially spreadable by the spreading elements.

With a practical embodiment of the invention it is proposed that the base body should be configured in box shape in such a way that the insertion opening is configured in an end plate of the base body and that the spreading elements extend from the insertion opening into the inside of the base body. This configuration is characterized by a structure that is robust and easy to manipulate.

Alternatively or in addition to the use of the at least one spring element, it is proposed with the invention that at least one spreading element of the pulling apparatus should have a springed configuration, such that, with the additional spring elasticity of the at least one spreading element, this spring elasticity can be adjusted by the dimensions of the spreading element and/or by its material properties in such a way that the spring elasticity of the at least one spreading element with springed configuration is configured as lesser than the spring force of the at least one spring element.

To ensure a more secure grip of the sheath on the spreading elements of the pulling apparatus, it is proposed with the invention that a holding bulge or holding recess for fastening the sheath should be configured on the distal end of the spreading elements and that on the proximal end of the sheath a surrounding bulge should be configured by which the sheath can be fastened on the spreading elements. The bulge of the sheath surrounding the proximal end serves, in addition, to be able to fasten the sheath in stable manner on the distal end of the surgical shaft instrument. The surrounding bulge serves in addition as tearing protection for the proximal area of the sheath.

To remove the instrument tip provided with the sheath from the pulling apparatus, it is proposed with the invention that in the end plate of the base body, laterally near the insertion opening, at least one removal opening connected with the insertion opening should be configured. Transferring the instrument tip provided with the sheath from the insertion opening into the removal opening with its greater diameter ensures that the sheath can also be removed again from the pulling apparatus in a manner that protects the material.

Advantageously, the inventive pulling apparatus itself is configured as an injection molding, which allows rapid and easy manufacture of the apparatus.

It is proposed with a second embodiment of the invention that the spreading elements should be mounted on one another so that they can pivot with respect to one another. In this embodiment no base body and no separate spring elements are required, so that this embodiment is characterized by its simple structure comprising only a few components.

According to a practical embodiment of this second embodiment, it is proposed that the spreading elements should be removably mounted on one another to make possible simple assembly and disassembly of the pulling apparatus.

With a preferred embodiment of the invention it is proposed that the pulling apparatus should consist of two spreading elements each configured as a half-shell with a U-shaped cross-section. The half-shell configuration of the spreading elements makes it possible to completely enclose the tool tip that is to be surrounded, using only two spreading elements.

To configure the spreading elements to pivot reciprocally, it is proposed with the invention that mounting pins and mounting recesses should be configured on the spreading elements. A mounting pin and a mounting recess are advantageously configured on each spreading element, so that it requires only one spreading element type, from which, used in a pair, a pulling apparatus can be installed.

To install the pulling apparatus as well as to remove the pulling apparatus from the sheathed tool tip, the spreading elements are configured to be detachable from one another. For this purpose it is proposed with the invention that the mounting pins and mounting recesses should be configured in such a way that the spreading elements can be detached from one another only in a single position pivoted with respect to one another. This is advantageously the position of greatest pivoting distance of the spreading elements with respect to one another, in order to avoid accidental detachment of the spreading elements during the sheathing phase.

To ensure a more secure grip of the sheath on the spreading elements of the pulling apparatus, it is proposed with the invention that a holding bulge for fastening the sheath should be configured on the distal end of the spreading elements and that on the proximal end of the sheath a surrounding bulge should be configured by which the sheath can be fastened on the spreading elements. The bulge of the sheath surrounding the proximal end serves, in addition, to be able to fasten the sheath in stable manner on the distal end of the surgical shaft instrument. The surrounding bulge serves in addition as tearing protection for the proximal area of the sheath.

Finally, it is proposed with the invention that the sheath consisting of an elastic material, in particular plastic, should be configured as open only on the proximal end. By configuring the sheath as a sleeve, open only on one end, made of an elastic material, it is possible, first, to completely enclose the tool of the surgical shaft instrument on the distal end and, second, to make possible, in addition, an actuation of the tool because of the elasticity of the sheath. In addition, because of the sheath the dilation mechanism is protected and penetration of tissue is prevented.

Further properties and advantages of the invention can be seen from the appended drawings, in which two embodiments of an inventive apparatus for mounting a sheath onto the distal end of a surgical shaft instrument are illustrated only as examples, without restricting the invention to these embodiments.

BRIEF DESCRIPTION OF THE DRAWINGS

FIG. 2b shows a partly cut-out side view of the depiction in FIG. 2a.

FIG. 4b shows a partly cut-out side view of the depiction in FIG. 4a.

FIG. 5b shows a side view of the depiction according to FIG. 5a.

DETAILED DESCRIPTION OF THE INVENTION

FIGS. 1 through 6b show a first embodiment of a pulling apparatus 1 for mounting a sheath 2 onto the distal end 3 of a surgical shaft instrument 4.

Figure 3:
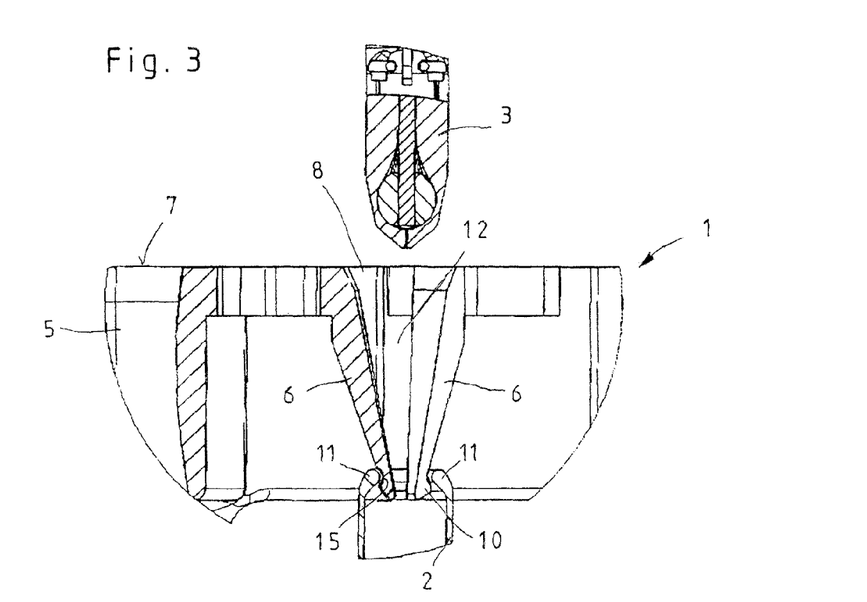
FIG. 3 shows an enlarged view of Detail III from FIG. 2b.

As can be seen in particular from FIG. 3, the illustrated first embodiment of the pulling apparatus 1 consists essentially of a box-shaped base body 5 and spreading elements 6, which extend from an upper end plate 7 of the base body 5 into the inside of the base body 5, such that an insertion opening 8 is configured between the spreading elements 6 in the end plate 7 of the base body 5 to receive the distal end 3 of the surgical shaft instrument 4 that forms the instrument tip 3.

In the illustrated embodiment, the pulling apparatus 1 comprises three spreading elements 6 that are mounted on the end plate 7 to tip with their proximal ends in such a way that the distal ends move essentially radially to the insertion opening 8 upon pivoting of the spreading elements 6. At least one spring element 9 is positioned between the individual spreading elements 6 in order to ensure uniform pivoting of the spreading elements 6.

The three spreading elements 6 in the illustrated embodiment are positioned radially at a 120 degree angle from one another, so that this arrangement corresponds to the arrangement of the jaw members of the instrument tip 3 that is to be sheathed, and thus a spreading of the jaw members of the instrument tip 3 is prevented upon insertion into the pulling apparatus 1.

Alternatively or in addition to using the at least one spring element 9, it is possible to configure at least one spreading element 6 as springed, such that with the additional spring elasticity of the spreading elements 6, said elasticity can be adjusted by the dimensions of the spreading elements 6 and/or by their material properties in such a way that the spring elasticity of the at least one springed spreading element 6 is configured as lesser than the spring force of the at least one spring element 9.

Alternatively to the illustrated embodiment, it is also possible to use only two spreading elements 6 or else more than three spreading elements 6.

As can be seen in particular from FIG. 3, on the distal end of the spreading elements 6, a holding bulge 10 is configured that points outward and on which the sheath 2 can be fastened to the spreading elements 6. For the same purpose, the sheath 2 comprises on its proximal end a surrounding bulge 11, which together with the holding bulge 10 of the spreading elements 6 ensures a secure grip of the sheath 2 on the pulling apparatus 1.

The detailed view of the spreading elements 6 according to FIG. 3 shows, along with the previously described configuration of the holding bulge 10 on the distal end to fasten the surrounding bulge 11 of the sheath 2 on the right-hand spreading element 6, an alternative embodiment on the spreading element 6 to the left of the illustration. In this alternative configuration, on the distal end of the spreading element 6, a holding recess 15 is configured in which the proximal-end surrounding bulge 11 of the sheath 2 can be fastened.

Application of a sheath 2 onto the distal end 3 of a surgical shaft instrument 4, in particular the tool tip of a dilation instrument, is described for the first embodiment of the pulling apparatus 1 hereinafter with reference to FIGS. 2a through 6b.

Figure 1:
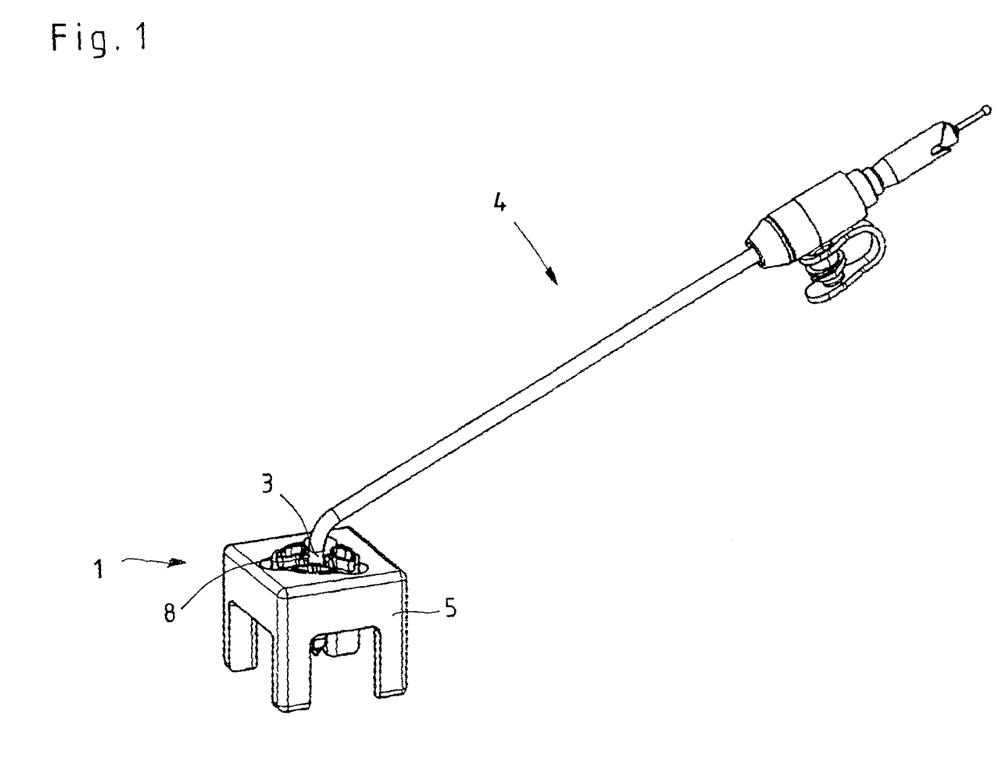
FIG. 1 shows a perspective view of a first embodiment of an inventive apparatus for mounting a sheath onto the distal end of a surgical shaft instrument.
Figure 2A:
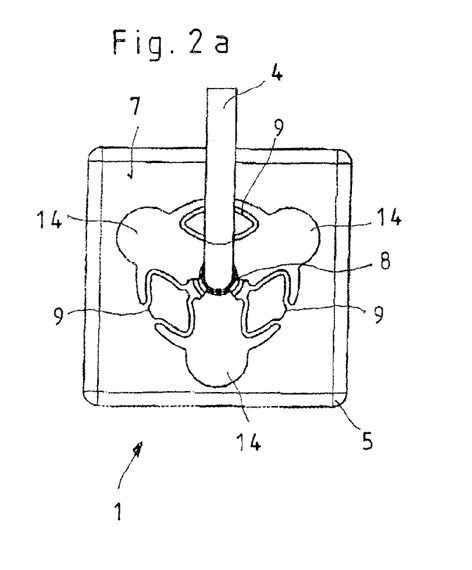
FIG. 2a shows an overhead view of the apparatus according to FIG. 1, depicting the starting position.
Figure 2B:
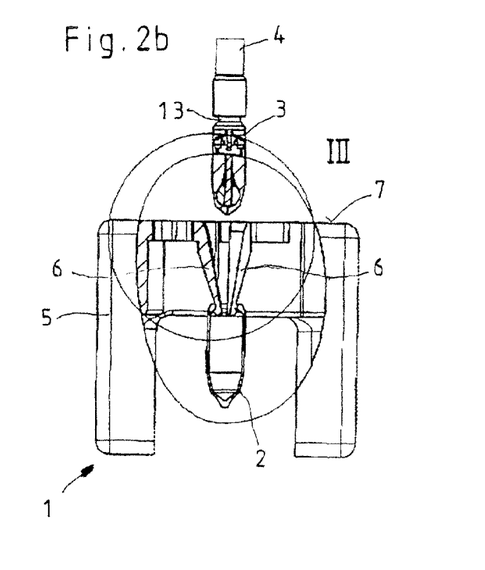

FIGS. 2a through 3 show the starting position before application of the sheath 2 on the instrument tip 3. First the sheath 2 is manually fastened on the distal end of the spreading element 6 of the pulling apparatus 1, as can be seen in particular from FIG. 3. In this starting position the surrounding bulge 11 of the sheath 2 open only on the proximal end overlaps the holding bulge 10 on the distal ends of the spreading elements 6. The insides of the spreading elements 6 form in the starting position a funnel-shaped insertion shaft 12, widening toward the insertion opening 8, for the instrument tip 3 that is to be sheathed.

To enclose the instrument tip 3 with the sheath 2, the surgical shaft instrument 4, with the instrument tip to the front, is now inserted vertically into the insertion opening 8 and the insertion shaft 12 formed by the spreading elements 6. On inserting the instrument tip 3 into the insertion shaft 12 that tapers toward the inside of the pulling apparatus 1, the spreading elements 6 are pressed radially outward by the instrument tip 3 against the force of the spring elements 9, leading to a radial widening of the proximal end of the sheath 2 that is fastened on the distal ends of the spreading elements 6, as can be seen in particular from FIG. 4b.

Figure 4A:
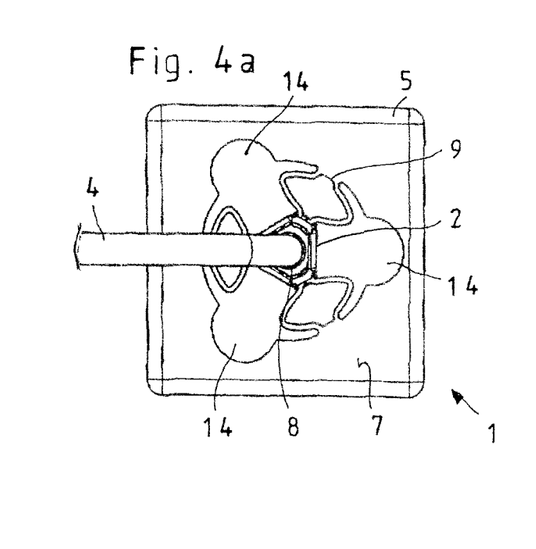
FIG. 4a shows an overhead view of the apparatus according to FIG. 1, depicting the insertion position.
Figure 4B:
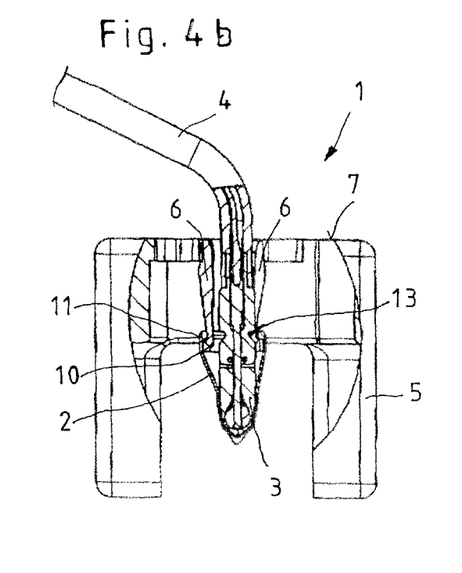
Figure 5A:
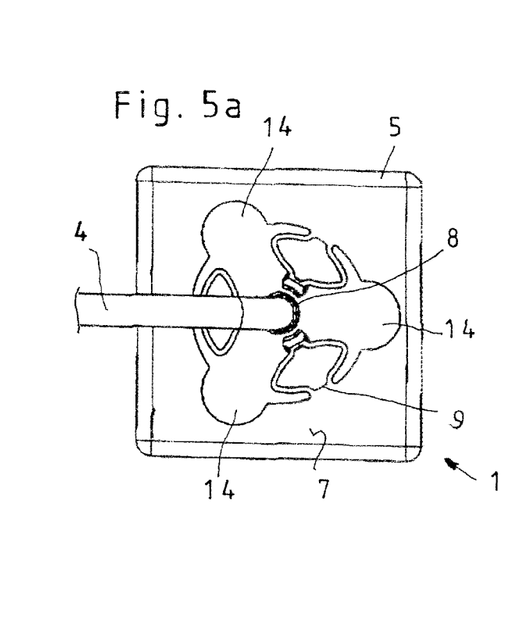
FIG. 5a shows an overhead view of the apparatus according to FIG. 1, depicting the sheathing position.
Figure 5B:
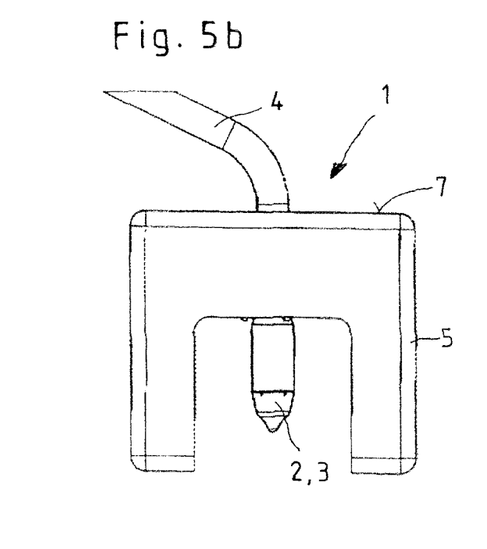

In this insertion position illustrated in FIGS. 4a and 4b, the instrument tip 3 is already positioned in the sheath 2, while the sheath 2 itself, on the other hand, is still fastened to the holding bulges 10 of the spreading elements 6 by its bulge 11 surrounding the proximal end.

To completely mount the sheath 2 on the instrument tip 3, the instrument tip 3 is pressed vertically downward farther into the interior of the pulling apparatus 1 until the bulge 11 surrounding the proximal end of the sheath 2 is pulled downward by the holding bulges 10 of the spreading elements 6 and comes to rest in a surrounding groove 13 on the distal end of the instrument tip 3 and thus fastens the sheath 2 in stable position on the instrument tip 3. This sheathing position can be seen from FIGS. 5a and 5b.

Figure 6A:
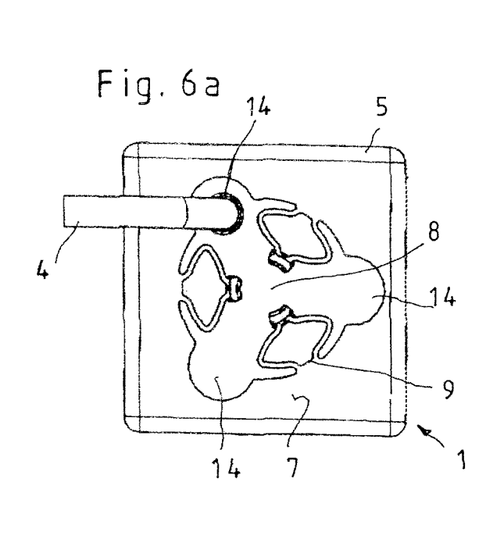
FIG. 6a shows an overhead view of the apparatus according to FIG. 1, depicting the removal position.
Figure 6B:
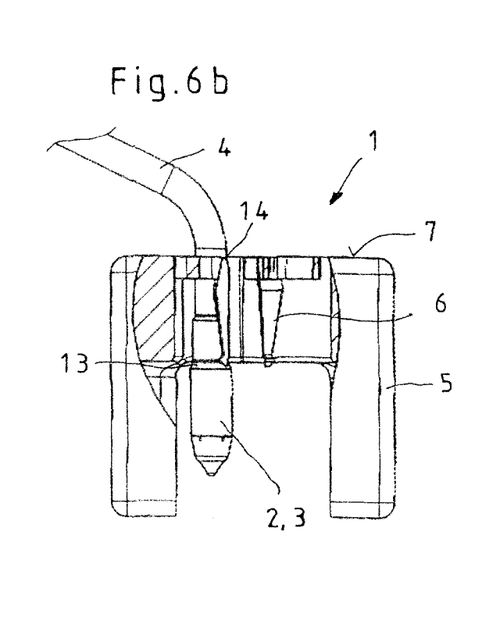
FIG. 6b shows a side view of a second embodiment of an inventive apparatus for mounting a sheath onto the distal end of a surgical shaft instrument, depicting the starting position.

Because, in drawing back the instrument tip 3 provided with the sheath 2 between the spreading elements 6 and through the insertion opening 8, there is the risk that the sheath 2 could be damaged or pulled downward, at least one removal opening 14, which is connected with the insertion opening 8 and is greater in diameter, is configured in the end plate 7 of the base body 5 laterally close to the insertion opening 8, for removing the instrument tip 3 provided with the sheath 2, as can be seen from FIGS. 6a and 6b.

In this removal position, the instrument tip 3 provided with the sheath 2 can now be withdrawn again from the pulling apparatus 1 easily and without risk.

Alternatively to the illustrated embodiment of the pulling apparatus 1 with a box-shaped base body 5 on which the spreading elements 6 are mounted so as to be able to pivot, it is also possible to configure the pulling apparatus 1 in forceps shape in such a way that the distal ends of the two branches of the forceps are configured as spreading elements 6 that extend at a right angle to the longitudinal axis of the forceps and on which the sheath 2 can be fastened. The radial widening of the proximal end of the sheath 2 or the radial spreading of the spreading elements 6 occurs in this embodiment through the actuation of the forceps' gripping parts on the proximal end.

Figure 7:
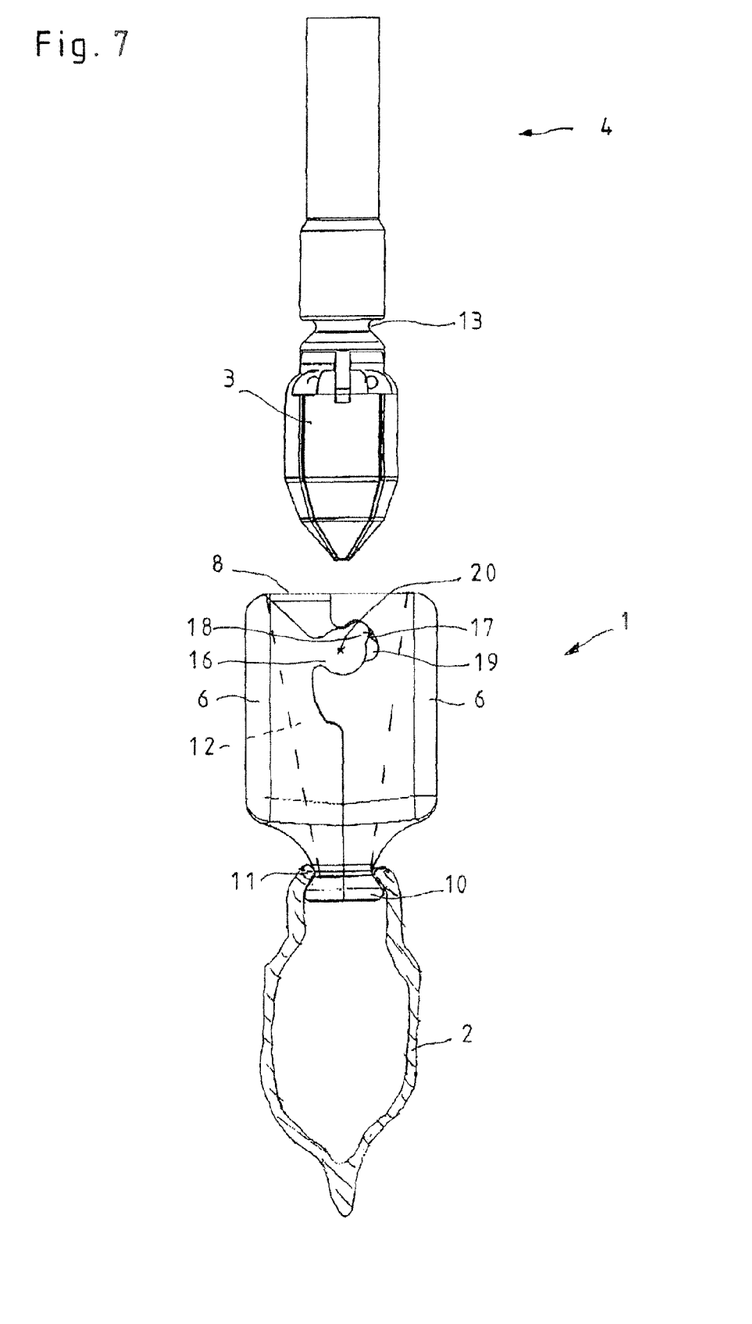
FIG. 7 shows a side view of a second embodiment of an inventive apparatus for mounting a sheath onto the distal end of a surgical shaft instrument, depicting the starting position.
Figure 8:
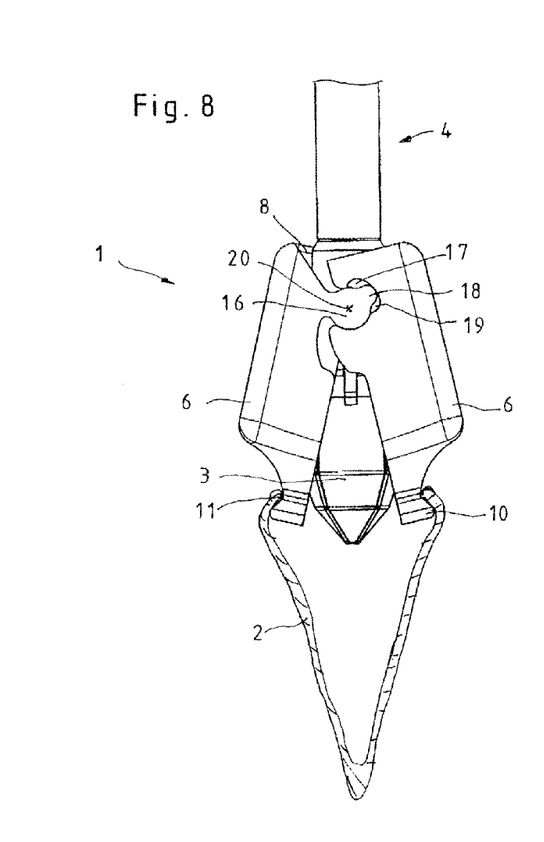
FIG. 8 shows an overhead view according to FIG. 7, depicting the insertion position.
Figure 9:
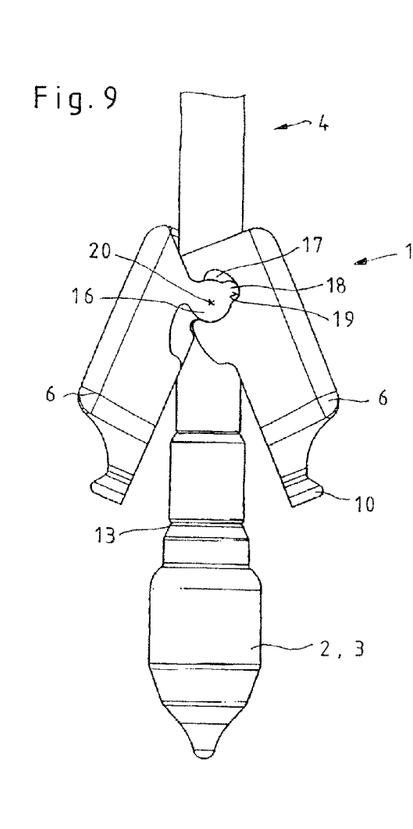
FIG. 9 shows a view according to FIG. 7, depicting the sheathing position.

FIGS. 7 through 9 show a second embodiment of the pulling apparatus 1, an apparatus configured as described above for mounting a sheath 2 on the distal end 3 of a surgical shaft instrument 4.

This second embodiment of the pulling apparatus 1 is distinguished from the first embodiment, described with reference to FIGS. 1 through 6b, essentially in that in this embodiment the spreading elements 6 are not mounted on a base body but rather immediately on one another.

In the illustrated embodiment, the pulling apparatus 1 consists of two spreading elements 6, which are configured as a half-shell with a U-shaped cross-section and which are mounted on one another so that they can pivot with respect to one another.

For reciprocal pivoting and reciprocal mounting on one another, mounting pins 16 and mounting recesses 17 are configured on the spreading elements 6 so that they grip into one another and around one another. Advantageously, on each spreading element 6 a mounting pin 16 and a mounting recess 17 are configured, so that the two spreading elements 6 that form the pulling apparatus 1 comprise a mirror-symmetrical shape. Because of this configuration, it requires only the configuration of one spreading arm type in order to be able to compose a pulling apparatus 1 from two spreading elements 6 without being able to confuse the left or right half-shell.

To install the pulling apparatus 1 as well as to remove the pulling apparatus 1 from the sheathed instrument tip 3, the spreading elements 6 are configured as detachable from one another. For this purpose the mounting pins 16 and the mounting recesses 17 are configured in such a way that the spreading elements 6 can be detached from one another only when pivoted with respect to one another in a single position. Advantageously this is the position in which the spreading elements 6 are pivoted away from one another at the greatest distance, as shown in FIG. 9, in order to avoid accidental release of the spreading elements 6 during the sheathing phase.

To allow this release to occur in only one particular pivoted position of the spreading elements 6, in the illustrated embodiment a protrusion 18 is formed on each mounting pin 16 to prevent withdrawal of the particular mounting pin 16 from the mounting recess 17 when the spreading elements 6 are in the non-pivoted or only partly pivoted position. Configured in each mounting recess 17 is a widening 19, into which the particular protrusion 18 of the mounting pin 16, only when in the foreseen release position, engages in such a way that the spreading elements 6 can be separated from one another.

The mounting of a sheath 2 onto the distal end 3 of a surgical shaft instrument 4, in particular the tool tip of a dilation instrument, is described hereinafter for the second embodiment of the pulling apparatus 1, with reference to FIGS. 7 through 9.

FIG. 7 shows a starting position before mounting the sheath 2 on the instrument tip 3. First, the sheath 2 is manually fastened on the distal ends of the spreading elements 6 of the pulling apparatus 1, as can be seen in particular from FIG. 7. In this starting position, the surrounding bulge 11 of the sheath 2 that is open only on the proximal end grips behind the holding bulge 10 on the distal ends of the spreading elements 6. The insides of the spreading elements 6, in the starting position, form a funnel-shaped insertion shaft 12 that widens toward the insertion opening 8 for the instrument tip 3 that is to be sheathed.

To enclose the instrument tip 3 with the sheath 2, the surgical shaft instrument 4, with the instrument tip 3 to the front, is inserted vertically into the insertion opening 8 and the insertion shaft 12 formed by the spreading elements 6. Upon inserting the instrument tip 3 into the insertion shaft 12, which tapers toward the inside of the pulling apparatus 1, the spreading elements 6 are pivoted outward with respect to one another on the distal end, through the pivot axis 20 formed by the mounting pins 16 mounted in the mounting recesses 17, thus causing a radial widening of the proximal end of the sheath 2 that is fastened on the distal ends of the spreading elements 6, as can be seen from FIG. 8.

In this insertion position shown in FIG. 8, the instrument tip 3 is already positioned partly in the sheath 2, but the sheath 2 itself is still fastened on the holding bulges 10 of the spreading elements 6 by its bulge 11 surrounding the proximal end.

To completely mount the sheath 2 on the instrument tip 3, the instrument tip 3 is pressed vertically downward, farther into the inside of the pulling apparatus 1 until the bulge 11 surrounding the proximal end of the sheath 2 is pulled downward by the holding bulges 10 of the spreading elements 6 and comes to rest in a surrounding groove 13 on the distal end of the instrument tip 3 and thus fastens the sheath 2 in stable position on the instrument tip 3. This sheathing position can be seen from FIG. 9.

In this sheathing position, in which the spreading elements 6 are pivoted at the greatest distance from one another, the spreading elements 6 can be separated from one another by withdrawing the mounting pins 16 from the mounting recesses 17 and can be removed from the sheathed instrument tip 3.

The apparatuses described above for mounting a sheath 2 onto the distal end 3 of a surgical shaft instrument 4 are characterized in that, with the easy handling and simple structure of the pulling apparatus 1, it becomes possible to position the sheath 2 on the instrument tip 3 of a surgical shaft instrument 4 quickly and without the risk of damage to the sheath 2.

The invention claimed is:

1. An apparatus for mounting a sheath onto a distal end of a surgical shaft instrument, the apparatus comprising:
    a base body;
    at least two spreading elements each having a proximal end and a distal end for fastening a sheath on the base body, the proximal ends of the at least two spreading elements being mounted to the base body such that the at least two spreading elements extend from the proximal ends into the base body, the at least two spreading elements being actuatable to radially widen at least a proximal end of the sheath; and
    an insertion opening formed in the base body between the proximal ends of the at least two spreading elements, the insertion opening providing an entry point to receive a distal end of a surgical shaft instrument and direct the distal end of the surgical shaft instrument into the widened proximal end of the sheath;
    the spreading elements being configured for transferring the sheath from the base body onto the distal end of the surgical shaft instrument.

2. The apparatus according to claim 1, wherein the spreading elements are mounted on the base body.

3. The apparatus according to claim 2, wherein the at least two spreading elements are mounted on the base body so that they are displaceable radially relative to the insertion opening.

4. The apparatus according to claim 2, wherein the base body is of box-shaped configuration so that the insertion opening is configured in an end plate of the base body and the spreading elements extend from the insertion opening into an interior of the base body.

5. The apparatus according to claim 2, wherein the spreading elements are pivotable radially against a force of at least one spring element.

6. The apparatus according to claim 5, wherein at least one of the at least two spreading elements is spring elastic.

7. The apparatus according to claim 6, wherein the spring elasticity of the at least one spring-elastic spreading element is less than the spring force of the at least one spring element.

8. The apparatus according to claim 4, wherein in the end plate of the base body, laterally close to the insertion opening, at least one removal opening connected with the insertion opening is configured for removal of the distal end of the surgical shaft instrument with the sheath mounted thereon.

9. The apparatus according to claim 1, wherein the base body is configured as an injection molding.

10. The apparatus according to claim 1, wherein a holding bulge or a holding recess for fastening the sheath is configured on the distal end of each spreading element.

11. The apparatus according to claim 1, wherein the at least two spreading elements grip a surrounding bulge of the sheath for fastening the sheath onto the spreading elements and to the distal end of the surgical shaft instrument.

12. The apparatus according to claim 4, wherein at least one removal opening connected with the insertion opening is configured in the end plate of the base body laterally close to the insertion opening and serves for removing the distal end of the surgical shaft instrument with the sheath mounted thereon.

13. The apparatus according to claim 1, wherein the sheath comprises an elastic material, the sheath having an opening only on the proximal end and being configured as an injection molding.

14. The apparatus according to claim 1, wherein the spreading elements are configured as injection moldings.

15. The apparatus according to claim 2, wherein at least one of the at least two spreading elements is spring elastic.

* * * * *